US012805551B2

(12) United States Patent
Ashokan et al.

(10) Patent No.: US 12,805,551 B2

(45) **Date of Patent: *Nov. 24, 2026**

(54) COMPOSITIONS FOR REDUCING OFF TASTES AND USES THEREOF

(71) Applicant: Firmenich SA, Satigny (CH)

(72) Inventors: Bharani Ashokan, Plainsboro, NJ (US); Muhammad Kizilbash, Plainsboro, NJ (US); Qingbo Ouyang, Plainsboro, NJ (US); Stuart Dash, Southall (GB); Patrice Merceret, Satigny (CH)

(73) Assignee: FIRMENICH SA, Satigny (CH)

( * ) Notice: Subject to any disclaimer, the term of this patent is extended or adjusted under 35 U.S.C. 154(b) by 420 days.

This patent is subject to a terminal disclaimer.

(21) Appl. No.: 17/995,734

(22) PCT Filed: May 27, 2021

(86) PCT No.: PCT/EP2021/064266

§ 371 (c)(1),
(2) Date: Oct. 7, 2022

(87) PCT Pub. No.: WO2021/244953

PCT Pub. Date: Dec. 9, 2021

(65) Prior Publication Data

US 2023/0157341 A1 May 25, 2023

Related U.S. Application Data

(60) Provisional application No. 63/034,095, filed on Jun. 3, 2020.

(30) Foreign Application Priority Data

Jun. 11, 2020 (EP) .................................... 20179560

(51) Int. Cl.

| | |
|---|---|
| ***A23L 27/00*** | (2016.01) |
| ***A61G 11/00*** | (2006.01) |
| ***A61K 8/60*** | (2006.01) |
| ***A61Q 11/00*** | (2006.01) |

(52) U.S. Cl.
CPC .............. *A23L 27/84* (2016.08); *A61G 11/00* (2013.01); *A61K 8/60* (2013.01)

(58) Field of Classification Search
CPC ......... A23L 27/84; A61K 8/60; A61K 8/4926; A61K 8/4973; A61Q 11/00
See application file for complete search history.

(56) References Cited

U.S. PATENT DOCUMENTS

| | | | | |
|---|---|---|---|---|
| 8,440,676 | B2 | 5/2013 | Shigemura et al. | |
| 8,541,421 | B2 * | 9/2013 | Tachdjian | A61P 5/00 544/278 |
| 9,732,071 | B2 | 8/2017 | Patron et al. | |
| 10,182,584 | B2 * | 1/2019 | Kulke | A61P 43/00 |
| 2007/0231278 | A1 | 10/2007 | Lee et al. | |
| 2014/0023750 | A1 * | 1/2014 | Purkayastha | C12P 19/56 426/549 |
| 2017/0087199 | A1 * | 3/2017 | Patron | A61K 31/381 |
| 2017/0119032 | A1 * | 5/2017 | Patron | A23L 27/204 |
| 2018/0133130 | A1 * | 5/2018 | Yuan | A61K 8/86 |

FOREIGN PATENT DOCUMENTS

| | | | |
|---|---|---|---|
| JP | 6530853 | B1 * | 6/2019 |
| KR | 20120057300 | A | 6/2012 |

OTHER PUBLICATIONS

Shigeto et al. Bioscience, biotechnology, and biochemistry 84.2 (2020): 421-427. (Year: 2020).*
International Search Report and Written Opinion for corresponding International Application No. PCT/EP2021/064266 dated Jul. 28, 2021 (13 pages).
Michael L. Schwieterman et al: "Strawberry Flavor: Diverse Chemical Compositions, a Seasonal Influence, and Effects on Sensory Perception", PLOS ONE, vol. 9, No. 2, Feb. 11, 2014, p. e88446.

* cited by examiner

*Primary Examiner* — Erik Kashnikow
*Assistant Examiner* — Janice Y Silverman

(57) ABSTRACT

The present disclosure generally provides taste-modifying compositions that reduce the off taste of alkali metal salts of peroxymonosulfate. In some aspects, the disclosure provides uses of such taste-modifying compositions to reduce the off taste of an alkali metal salt of peroxymonosulfate, such as potassium peroxymonosulfate. In some other aspects, the disclosure provides compositions (such as comestible compositions or oral care compositions), which comprise an alkali metal salt of peroxymonosulfate and a taste-modifying composition of the present disclosure. In some embodiments, such compositions are in the form of a food product, a beverage product, or an oral care product, such as a toothpaste, a mouthwash, and the like.

4 Claims, No Drawings

COMPOSITIONS FOR REDUCING OFF TASTES AND USES THEREOF

CROSS-REFERENCE TO RELATED APPLICATIONS

The present application is a U.S. national phase entry under 35 U.S.C. § 371 of PCT Application No. PCT/EP2021/064266, filed May 27, 2021, which claims the benefit of priority of U.S. Provisional Application No. 63/034,095, filed Jun. 3, 2020, and European Patent Application No. 20179560.6, filed Jun. 11, 2020. The entire contents of these applications are explicitly incorporated herein by this reference.

TECHNICAL FIELD

The present disclosure generally provides taste-modifying compositions that reduce the off taste of alkali metal salts of peroxymonosulfate. In some aspects, the disclosure provides uses of such taste-modifying compositions to reduce the off taste of an alkali metal salt of peroxymonosulfate, such as potassium peroxymonosulfate. In some other aspects, the disclosure provides compositions (such as comestible compositions or oral care compositions), which comprise an alkali metal salt of peroxymonosulfate and a taste-modifying composition of the present disclosure. In some embodiments, such compositions are in the form of a food product, a beverage product, or an oral care product, such as a toothpaste, a mouthwash, tooth-whitening compositions, and the like.

DESCRIPTION OF RELATED ART

The taste system provides sensory information about the chemical composition of the external world. Taste transduction is one of the more sophisticated forms of chemically triggered sensation in animals. Signaling of taste is found throughout the animal kingdom, from simple metazoans to the most complex of vertebrates. Mammals are believed to have five basic taste modalities: sweet, bitter, sour, salty, and umami.

Alkali metal salts of peroxymonosulfate, such as potassium salts, are commonly used in oral care products as a whitening agent. The inclusion of such salts can lead to off tastes that users find unpleasant. Limiting the concentration of such salts is a potential strategy for reducing the any unpleasant taste. But it may often be desirable to include such salts at higher concentrations to have an improved effect.

Therefore, there is a need to discover new compositions that can effectively reduce the perception of off tastes that humans experience in connection with alkali metal salts of peroxymonosulfate.

SUMMARY

The present disclosure relates to the discovery that certain compositions exhibit a unexpected effectiveness at reducing the perception of saltiness caused by the presence of sodium cations in food, beverage, or oral care products.

In a first aspect, the disclosure provides taste-modifying compositions, the compositions comprising: (a) 4-amino-5,6-dimethylthieno[2,3-d]pyrimidin-2(1H)-one, or a salt thereof; and (b) a lactone. In some embodiments, the composition comprises a sweetener, such as sucralose. In some further embodiments, the composition comprises glucosylated natural steviol glycosides. In some further embodiments, the composition comprises a flavoring.

In a second aspect, the disclosure provides uses of the taste-modifying composition of the first aspect to reduce an off taste of a flavored product. In some embodiments, the flavored product is a food product or a beverage product. In some other embodiments, the flavored product is an oral care product, such as a toothpaste, a mouthwash, or a tooth-whitening composition.

In a third aspect, the disclosure provides methods for reducing an off taste of a flavored product, the method comprising introducing a taste-modifying composition of the first aspect to a flavored product. In some embodiments, the flavored product is a food product or a beverage product. In some other embodiments, the flavored product is an oral care product, such as a toothpaste, a mouthwash, or a teeth-whitening product. In some embodiments, the flavored product comprises an alkali metal salt of peroxymonosulfate, such as potassium peroxymonosulfate.

In a fourth aspect, the disclosure provides flavored products comprising a taste-modifying composition of the first aspect and comprises an alkali metal salt of peroxymonosulfate, such as potassium peroxymonosulfate. In some embodiments, the flavored product is a food product or a beverage product. In some other embodiments, the flavored product is an oral care product, such as a toothpaste, a mouthwash, or a teeth-whitening product.

Further aspects, and embodiments thereof, are set forth below in the Detailed Description, the Drawings, the Abstract, and the Claims.

DETAILED DESCRIPTION

The following Detailed Description sets forth various aspects and embodiments provided herein. The description is to be read from the perspective of the person of ordinary skill in the relevant art. Therefore, information that is well known to such ordinarily skilled artisans is not necessarily included.

Definitions

The following terms and phrases have the meanings indicated below, unless otherwise provided herein. This disclosure may employ other terms and phrases not expressly defined herein. Such other terms and phrases have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary A "sweetener", "sweet flavoring agent", "sweet flavor entity", or "sweet compound" herein refers to a compound or ingestibly acceptable salt thereof that elicits a detectable sweet flavor in a subject, e.g., a compound that activates a T1R2/T1R3 receptor in vitro.

An "off taste" refers to a taste that humans generally perceive as unpleasant, such as a bitter taste, a metallic taste, a burning taste, an aldehydic taste, or any combination thereof.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "optionally" means that the subsequently described event(s) may or may not occur. In some embodiments, the optional event does not occur. In some other embodiments, the optional event does occur one or more times.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

Other terms are defined in other portions of this description, even though not included in this subsection.

Taste-Modifying Compositions

In at least one aspect, the disclosure provides a taste-modifying composition, the composition comprising: (a) 4-amino-5,6-dimethylthieno[2,3-d]pyrimidin-2(1H)-one, or a salt thereof; and (b) a lactone.

As noted above, the taste-modifying composition comprises 4-amino-5,6-dimethylthieno[2,3-d]pyrimidin-2(1H)-one, or any suitable salt thereof can be used. In some embodiments, the taste-modifying compositions disclosed herein comprise the hydrochloride salt of 4-amino-5,6-dimethylthieno[2,3-d]pyrimidin-2(1H)-one.

The taste-modifying composition also comprises a lactone. Any suitable lactone or combination of lactones can be used. In some embodiments, the lactone comprises a lactone ring having from 3 to 8 members in the ring, such as a 3-membered lactone ring, a 4-membered lactone ring, a 5-membered lactone ring, a 6-membered lactone ring, a 7-membered lactone ring, or an 8-membered lactone ring.

In some embodiments, the lactone comprises a 5-membered lactone ring with or without an unsaturated bond (excluding the unsaturation in the oxo substituent on the ring), such as a carbon-carbon double bond. In some embodiments, the lactone comprises a 5-membered lactone ring including at least one unsaturated bond (for example, one carbon-carbon double bond). Non-limiting examples of lactones comprising a 5-membered lactone ring having at least one unsaturated bond include angelica lactone alpha, angelica lactone beta, mint lactone, 5,5-dimethyl-2(5H)-furanone, 5-ethyl-2(5H)-furanone, 5-pentyl-2(5H)-furanone, 5-hexyl-2(5H)-furanone, 5-pentyl-2(3H)-furanone, 4-methyl-3-pentyl-2(5H)-furanone, and 2(5H)-furanone. In some embodiments, the lactone comprises a 5-membered lactone ring without any unsaturated bonds. Non-limiting examples of such lactones include butyrolactone gamma, valerolactone gamma, hexalactone gamma, heptalactone gamma, octalactone gamma, undecalactone gamma, decalactone gamma, dihydrojasmone lactone, and dihydromintlactone (3,6-dimethyl-hexahydro-2(3H)-benzofuranone). In some embodiments, the lactone is dihydromintlactone.

In some embodiments, the lactone comprises a 6-membered lactone ring with or without an unsaturated bond. In some embodiments, the lactone comprises a 6-membered lactone ring including at least one unsaturated bond. Non-limiting examples of lactones comprising a 6-membered lactone ring having at least one unsaturated bond include δ-2-decenolactone, coumarin, and 6-methylcoumarin. In some other embodiments, the lactone includes a 6-membered lactone ring without any unsaturated bonds. Non-limiting examples of lactones including a 6-membered lactone ring without any unsaturated bonds include decalactone delta, dodecalactone delta, and cyclohexyl lactone.

The taste-modifying composition can include certain additional ingredients. For example, in come embodiments, the taste-modifying composition comprises: (c) glucosylated natural steviol glycosides. As used herein, the term "natural steviol glycosides" refers to steviol glycosides naturally found in the plants of the species *Stevia rebaudiana, Stevia phlebophylla*, or *Rubus chingii*. Such compounds are glycosides of the diterpene, steviol. Some non-limiting examples include stevioside, rebaudioside A, rebaudioside C, dulcoside A, and the like. As used herein, the term "glucosylated natural steviol glycosides" refers to compounds obtained by the enzymatic glucosylation of natural steviol glycosides to increase the degree of glucosylation. As used herein, the term "GSG" is used interchangeably with "glucosylated natural steviol glycoside."

In embodiments in which GSGs are present, any suitable GSGs may be used. Thus, the GSGs can have any suitable degree of additional glucosylation, and ant suitable type of glucosylation. In some embodiments, the GSGs used in the taste-modifying composition have a degree of glucosylation of at least 1.0, meaning that at least one mole of glucose has been enzymatically added to the natural steviol glycosides per mole of natural steviol glycoside. In some other embodiments, the GSGs used in the taste-modifying composition have a degree of glucosylation of at least 1.1, or at least 1.2, or at least 1.3, or at least 1.4, or at least 1.5, or at least 1.6, or at least 1.7, or at least 1.8, or at least 1.9, or at least 2.0, or at least 2.1, or at least 2.2, or at least 2.3, or at least 2.4, or at least 2.5. The glucosylation can be of any suitable type. For example, in some embodiments, the glucose enzymatically added to the natural steviol glycosides is alpha-glucose, beta-glucose, or a combination thereof. In some embodiments, the glucose enzymatically added to the natural steviol glycosides is alpha-glucose. In some embodiments, the glucose enzymatically added to the natural steviol glycosides is beta-glucose. In some embodiments, the glucose enzymatically added to the natural steviol glycosides is a combination of alpha-glucose and beta-glucose. The glucose added by enzymatic glucosylation can be incorporated via any suitable connection. Typically, the added glucose units connect to other glucose glucose units already present on the natural steviol glycoside. In some embodiments, the enzymatically added glucose units are added via 1,6 linkages, meaning that the glucose units add via the 1-position of the added glucose unit and the 6-position of the glucose unit already present on the natural steviol glycoside. In some other embodiments, the enzymatically added glucose units are added via a 1,4 linkages. In some other embodiments, the enzymatically added glucose units are added via a 1,2 linkages.

In some embodiments, the taste modifying compositions comprise: (d) a sweetener, such as a low-calorie or zero-calorie sweetener. Examples of suitable sweeteners are set forth in greater detail below. In some embodiments, the sweetener is sucralose, which refers to 1,6-dichloro-1,6-dideoxy-β-D-fructofuranosyl-4-chloro-4-deoxy-α-D-galactopyranoside.

The compounds of the groups (a), (b), (c), and (d) can be present in the taste-modifying composition in any suitable ratios to each other. In some embodiments where compounds of class (a) and compounds of class (b) are both present, the weight-weight ratio of compounds of class (a) and compounds of class (b) ranges from 1:1 to 5:1, or from 2:1 to 4:1. In some embodiments where compounds of class (a) and compounds of class (c) are both present, the weight-weight ratio of compounds of class (a) and compounds of class (c) ranges from 0.8:1.0 to 2.4:1.0, or from 1.2:1.0 to 2.0:1.0. In some embodiments where compounds of class (a) and compounds of class (d) are both present, the weight-weight ratio of compounds of class (a) and compounds of class (d) ranges from 1:12 to 1:3, or from 1:8 to 1:4. In some embodiments where compounds of class (b) and compounds of class (c) are both present, the weight-weight ratio of compounds of class (b) and compounds of class (c) ranges from 1:4 to 3:2, or from 1:3 to 1:1. In some embodiments where compounds of class (b) and compounds of class (d) are both present, the weight-weight ratio of compounds of class (b) and compounds of class (d) ranges from 1:40 to 1:10, or from 1:30 to 1:12. In some embodiments where compounds of class (c) and compounds of class (d) are both present, the weight-weight ratio of compounds of class (c) and compounds of class (d) ranges from 1:25 to 1:2, or from 1:20 to 1:5.

The taste-modifying composition can contain other suitable ingredients, such as additional sweeteners, flavorings, carriers, binders, cooling agents, and the like.

For example, in some embodiments, the taste-modifying composition comprises a caloric sugar, such as sucrose, glucose, fructose (e.g., in the form of high-fructose corn syrup), or any combination thereof. In some embodiments, the taste-modifying composition comprises one or more rebaudiosides (such as rebaudioside A, rebaudioside D, rebaudioside E, rebaudioside M, or any combination thereof). In general, the concentrations of rebaudiosides (such as rebaudioside A) would be about 20 to 50 times higher than those set forth above for sucralose. In some embodiments, the taste-modifying composition comprises one or more high-intensity artificial sweeteners, such as acefulfame potassium, aspartame, cyclamate, neotame, and the like. When any such artificial high-intensity sweeteners are present in the taste-modifying composition, their concentration would be about the same as those set forth above for sucralose. In some other embodiments, the taste-modifying compositions comprise one or more low-calorie carbohydrates or sugar alcohols, such as allulose, xylitol, erythritol, and the like. In some other embodiments, the taste-modifying compositions comprise mogrosides, for example, as monk fruit juice or extract, or as one or more of mogroside III, mogroside IV, mogroside V, siamenoside I, isomogroside V, mogroside $IV_E$, isomogroside $IV_E$, isomogroside IV, mogroside $III_E$, 11-oxomogroside V, the 1,6-alpha isomer of siamenoside I, and any combinations thereof. Additional mogroside compounds that may be suitably included in the taste-modifying composition are described in U.S. Patent Application Publication No. 2017/0119032.

Various other sweeteners may also be included in the taste-modifying compositions. Non-limiting examples include D-psicose, L-ribose, D-tagatose, L-glucose, L-fucose, L-arbinose, D-turanose, D-leucrose, isomalt, lactitol, mannitol, sorbitol, maltodextrin, saccharin, alitame, cyclamic acid, tagatose, maltose, galactose, mannose, lactose, D-tryptophan, glycine, maltitol, lactitol, isomalt, hydrogenated starch hydrolyzate (HSH), chemically modified mogrosides (such as glucosylated mogrosides), carrelame and other guanidine-based sweeteners, honey, Jerusalem artichoke syrup, licorice root, luo han guo (fruit, powder, or extracts), lucuma (fruit, powder, or extracts), maple sap (including, for example, sap extracted from *Acer saccharum, Acer nigrum, Acer rubrum, Acer saccharinum, Acer platanoides, Acer negundo, Acer macrophyllum, Acer grandidentatum, Acer glabrum, Acer mono*), maple syrup, maple sugar, walnut sap (including, for example, sap extracted from *Juglans cinerea, Juglans nigra, Juglans ailatifolia, Juglans regia*), birch sap (including, for example, sap extracted from *Betula papyrifera, Betula alleghaniensis, Betula lenta, Betula nigra, Betula populifolia, Betula pendula*), sycamore sap (such as, for example, sap extracted from *Platanus occidentalis*), ironwood sap (such as, for example, sap extracted from *Ostrya virginiana*), mascobado, molasses (such as, for example, blackstrap molasses), molasses sugar, monatin, monellin, cane sugar (also referred to as natural sugar, unrefined cane sugar, or sucrose), palm sugar, panocha, piloncillo, rapadura, raw sugar, rice syrup, sorghum, sorghum syrup, cassava syrup (also referred to as tapioca syrup), thaumatin, yacon root, malt syrup, barley malt syrup, barley malt powder, beet sugar, cane sugar, crystalline juice crystals, caramel, carbitol, carob syrup, castor sugar, hydrogenated starch hydrolates, hydrolyzed can juice, hydrolyzed starch, invert sugar, anethole, arabinogalactan, arrope, syrup, P-4000, acesulfame potassium (also referred to as acesulfame K or ace-K), alitame (also referred to as aclame), advantame, aspartame, baiyunoside, neotame, benzamide derivatives, bernadame, canderel, carrelame and other guanidine-based sweeteners, vegetable fiber, corn sugar, coupling sugars, curculin, cyclamates, cyclocarioside I, demerara, dextran, dextrin, diastatic malt, dulcin, sucrol, valzin, dulcoside A, dulcoside B, emulin, enoxolone, maltodextrin, saccharin, estragole, ethyl maltol, glucin, gluconic acid, glucono-lactone, glucosamine, glucoronic acid, glycerol, glycine, glycyphillin, glycyrrhizin, glycyrrhetic acid monoglucuronide, golden sugar, yellow sugar, golden syrup, granulated sugar, gynostemma, hernandulcin, isomerized liquid sugars, jallab, chicory root dietary fiber, kynurenine derivatives (including N'-formyl-kynurenine, N'-acetyl-kynurenine, 6-chloro-kynurenine), galactitol, litesse, ligicane, lycasin, lugduname, guanidine, falernum, mabinlin I, mabinlin II, maltol, maltisorb, maltodextrin, maltotriol, mannosamine, miraculin, mizuame, mogrosides (including, for example, mogroside IV, mogroside V, and neomogroside), mukurozioside, nano sugar, naringin dihydrochalcone, neohesperidine dihydrochalcone, nib sugar, nigero-oligosaccharide, norbu, orgeat syrup, osladin, pekmez, pentadin, periandrin I, perillaldehyde, perillartine, petphyllum, phenylalanine, phlomisoside I, phlorodizin, phyllodulcin, polyglycitol syrups, polypodoside A, pterocaryoside A, pterocaryoside B, rebiana, refiners syrup, rub syrup, rubusoside, selligueain A, shugr, siamenoside I, siraitia grosvenorii, soybean oligosaccharide, Splenda, SRI oxime V, steviol glycoside, steviolbioside, stevioside, strogins 1, 2, and 4, sucronic acid, sucrononate, sugar, suosan, phloridzin, superaspartame, tetrasaccharide, threitol, treacle, trilobtain, tryptophan and derivatives (6-trifluoromethyl-tryptophan, 6-chloro-D-tryptophan), vanilla sugar, volemitol, birch syrup, aspartame-acesulfame, assugrin, and combinations or blends of any two or more thereof.

The taste-modifying compositions can, in certain embodiments, comprise any additional ingredients or combination of ingredients as are commonly used in food and beverage products, including, but not limited to:

- acids, including, for example citric acid, phosphoric acid, ascorbic acid, sodium acid sulfate, lactic acid, or tartaric acid;
- bitter ingredients, including, for example caffeine, quinine, green tea, catechins, polyphenols, green robusta coffee extract, green coffee extract, potassium chloride, menthol, or proteins (such as proteins and protein isolates derived from plants, algae, or fungi);
- coloring agents, including, for example caramel color, Red #40, Yellow #5, Yellow #6, Blue #1, Red #3, purple carrot, black carrot juice, purple sweet potato, vegetable juice, fruit juice, beta carotene, turmeric curcumin, or titanium dioxide;
- preservatives, including, for example sodium benzoate, potassium benzoate, potassium sorbate, sodium metabisulfate, sorbic acid, or benzoic acid;
- antioxidants including, for example ascorbic acid, calcium disodium EDTA, alpha tocopherols, mixed tocopherols, rosemary extract, grape seed extract, resveratrol, or sodium hexametaphosphate;
- vitamins or functional ingredients including, for example resveratrol, Co-Q10, omega 3 fatty acids, theanine, choline chloride (citocoline), fibersol, inulin (chicory root), taurine, *Panax ginseng* extract, guanana extract, ginger extract, L-phenylalanine, L-carnitine, L-tartrate, D-glucoronolactone, inositol, bioflavonoids, Echinacea, *Ginko biloba*, yerba mate, flax seed oil, *Garcinia cambogia* rind extract, white tea extract, ribose, milk thistle extract, grape seed extract, pyrodixine HCl (vitamin B6), cyanoobalamin (vitamin B12), niacinamide (vitamin B3), biotin, calcium lactate, calcium pantothenate (pantothenic acid), calcium phosphate, calcium carbonate, chromium chloride, chromium polynicotinate, cupric sulfate, folic acid, ferric pyrophosphate, iron, magnesium lactate, magnesium carbonate, magnesium sulfate, monopotassium phosphate, monosodium phosphate, phosphorus, potassium iodide, potassium phosphate, riboflavin, sodium sulfate, sodium gluconate, sodium polyphosphate, sodium bicarbonate, thiamine mononitrate, vitamin D3, vitamin A palmitate, zinc gluconate, zinc lactate, or zinc sulphate;
- clouding agents, including, for example ester gun, brominated vegetable oil (BVO), or sucrose acetate isobutyrate (SAIB);
- buffers, including, for example sodium citrate, potassium citrate, or salt;
- flavors, including, for example propylene glycol, ethyl alcohol, glycerine, gum Arabic (gum acacia), maltodextrin, modified corn starch, dextrose, natural flavor, natural flavor with other natural flavors (natural flavor WONF), natural and artificial flavors, artificial flavor, silicon dioxide, magnesium carbonate, or tricalcium phosphate; or
- starches and stabilizers, including, for example pectin, xanthan gum, carboxylmethylcellulose (CMC), polysorbate 60, polysorbate 80, medium chain triglycerides, cellulose gel, cellulose gum, sodium caseinate, modified food starch, gum Arabic (gum acacia), inulin, or carrageenan.

The taste-modifying compositions can have any suitable pH when dissolved or suspended in aqueous media, e.g., from lower pH to neutral pH. The lower and neutral pH includes, but is not limited to, a pH from 1.5 to 9.0, or from 2.5 to 8.5; from 3.0 to 8.0; from 3.5 to 7.5; and from 4.0 to 7.

The taste-modifying compositions set forth according to any of the foregoing embodiments, also include, in certain embodiments, one or more additional flavor-modifying compounds, such as compounds that enhance sweetness (e.g., hesperetin, naringenin, etc.), compounds that block bitterness, compounds that enhance umami, compounds that reduce sourness or licorice taste, compounds that enhance saltiness, compounds that enhance a cooling effect, or any combinations of the foregoing.

In some embodiments, taste-modifying compositions disclosed herein comprise one or more sweetness enhancing compounds. Such sweetness enhancing compounds include, but are not limited to, naturally derived compounds, such as hesperitin, naringenin, rhoifolin, glucosylated steviol glycosides, licorice-derived glucuronates, aromadendrin-3-O-acetate, or other like flavonols, or flavonoids, or synthetic compounds, such as any compounds set forth in U.S. Pat. Nos. 8,541,421; 8,815,956; 9,834,544; 8,592,592; 8,877,922; 9,000,054; and 9,000,051, as well as U.S. Patent Application Publication No. 2017/0119032. Some suitable examples include: 3-((4-amino-2,2-dioxo-1H-benzo[c][1,2,6]thiadiazin-5-yl)oxy)-2,2-dimethyl-N-propyl-propanamide, N-(1-((4-amino-2,2-dioxo-1H-benzo[c][1,2,6]-thiadiazin-5-yl)oxy)-2-methyl-propan-2-yl)isonicotinamide, or any combination thereof.

In some further embodiments, taste-modifying compositions disclosed herein comprise one or more other umami or kokumi enhancing compounds. Such umami enhancing compounds include, but are not limited to, naturally derived compounds, such as ericamide, or synthetic compounds, such as any compounds set forth in U.S. Pat. Nos. 8,735,081; 8,124,121; and 8,968,708.

In some further embodiments, taste-modifying compositions disclosed herein comprise one or more cooling enhancing compounds. Such cooling enhancing compounds include, but are not limited to, naturally derived compounds, such as menthol or analogs thereof, or synthetic compounds, such as any compounds set forth in U.S. Pat. Nos. 9,394,287 and 10,421,727.

In some further embodiments, taste-modifying compositions disclosed herein comprise one or more bitterness blocking compounds. Such bitterness blocking compounds include, but are not limited to, naturally derived compounds, such as menthol or analogs thereof, or synthetic compounds, such as any compounds set forth in U.S. Pat. Nos. 8,076,491; 8,445,692; and 9,247,759.

In some further embodiments, taste-modifying compositions disclosed herein comprise one or more mouthfeel modifying compounds. Such mouthfeel modifying compounds include, but are not limited to, tannins, cellulosic materials, bamboo powder, and the like.

In some further embodiments, taste-modifying compositions disclosed herein comprise one or more flavor masking compounds. Such flavor masking compounds include, but are not limited to, cellulosic materials, materials extracted from fungus, materials extracted from plants, citric acid, carbonic acid (or carbonates), and the like.

The taste-modifying compositions disclosed herein can, in certain embodiments, comprise cyclosal. When cyclosal is present, it is present at a relative concentration similar to that of the lactones.

The taste-modifying composition can be in any suitable form. For example, in some embodiments, the composition is in the form of a solid, such as a solid powder. In some such embodiments, the composition also comprises a solid carrier, such as a carbohydrate. In some other embodiments, the taste-modifying composition is in the form of a liquid solution or suspension. Such a liquid form can be aqueous or non-aqueous, or can also be an emulsion, such as an oil-in-water or water-in-oil emulsion. In some embodiments, the taste-modifying composition is incorporated into a flavored product, such as a food or beverage product, or an oral care product, such as a toothpaste or mouthwash.

In some embodiments, the taste-modifying composition comprises one or more flavorings, or any other additives described in H. Mitchell, Sweeteners and Sugar Alternatives in Food Technology, Blackwell Publishing Ltd, 2006. As used herein, the term "flavorings" includes those flavors known to the skilled person, such as natural and artificial flavors. These flavorings may be chosen from synthetic flavor oils and flavoring aromatics or oils, oleoresins and extracts derived from plants, leaves, flowers, fruits, and so forth, and combinations thereof. Non-limiting representative flavor oils include spearmint oil, cinnamon oil, oil of wintergreen (methyl salicylate), peppermint oil, Japanese mint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, yazu, sudachi, and fruit essences including apple, pear, peach, grape, blueberry, strawberry, raspberry, cherry, plum, pineapple, watermelon, apricot, banana, melon, apricot, ume, cherry, raspberry, blackberry, tropical fruit, mango, mangosteen, pomegranate, papaya and so forth. Other potential flavors include a milk flavor, a butter flavor, a cheese flavor, a cream flavor, and a yogurt flavor; a vanilla flavor; tea or coffee flavors, such as a green tea flavor, a oolong tea flavor, a tea flavor, a cocoa flavor, a chocolate flavor, and a coffee flavor; mint flavors, such as a peppermint flavor, a spearmint flavor, and a Japanese mint flavor; spicy flavors, such as an asafetida flavor, an ajowan flavor, an anise flavor, an angelica flavor, a fennel flavor, an allspice flavor, a cinnamon flavor, a camomile flavor, a mustard flavor, a cardamom flavor, a caraway flavor, a cumin flavor, a clove flavor, a pepper flavor, a coriander flavor, a sassafras flavor, a savory flavor, a Zanthoxyli Fructus flavor, a perilla flavor, a juniper berry flavor, a ginger flavor, a star anise flavor, a horseradish flavor, a thyme flavor, a tarragon flavor, a dill flavor, a capsicum flavor, a nutmeg flavor, a basil flavor, a marjoram flavor, a rosemary flavor, a bayleaf flavor, and a wasabi (Japanese horseradish) flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor. These flavoring agents may be used in liquid or solid form and may be used individually or in admixture. Commonly used flavors include mints such as peppermint, menthol, spearmint, artificial vanilla, cinnamon derivatives, and various fruit flavors, whether employed individually or in admixture. Flavors may also provide breath freshening properties, particularly the mint flavors when used in combination with cooling agents.

Flavors may also provide breath freshening properties, particularly the mint flavors when used in combination with cooling agents. These flavorings may be used in liquid or solid form and may be used individually or in admixture. Other useful flavorings include aldehydes and esters such as cinnamyl acetate, cinnamaldehyde, citral diethylacetal, dihydrocarvyl acetate, eugenyl formate, p-methylamisol, and so forth may be used. Generally, any flavoring or food additive such as those described in Chemicals Used in Food Processing, publication 1274, pages 63-258, by the National Academy of Sciences, may be used.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, and mixtures thereof. These listings of flavorings are merely exemplary and are not meant to limit either the term "flavoring" or the scope of the disclosure generally.

In certain embodiments, mint flavorings, including menthol and related compounds, or other breath-freshening compounds, can be combined with cooling agents, such as those set forth in U.S. Pat. Nos. 9,394,287 and 9,732,071. Additional examples of cooling agents include 5-methyl-2-(propane-2-yl)cyclohexyl-N-ethyloxamate, N-ethyl-p-menthane carboxamide (WS-3, also referred to as menthane-3-carboxylic acid-N-ethyl amide), N-2,3-trimethyl-2-isopropyl butane amide (WS-23), menthyl lactate (Frescolat® ML), menthone glycerine acetal (Frescolat® MGA), mono-menthyl succinate (Physcool®), mono-menthyl glutarate, 0-menthyl-glycerine, menthyl-N,N-dimethyl succinamate, N-(4-cyano methyl phenyl)-p-menthane carboxamide, N-(2-(pyridin-2-yl)ethyl)-3-p-menthane carboxamide, menthol and menthol derivatives (e.g. L-menthol, D-menthol, racemic menthol, isomenthol, neoisomenthol, neomenthol) menthyl ether (e.g. (I-menthoxy)-1,2-propanediol, (I-menthoxy)-2-methyl-1,2-propanediol, 1-menthyl-methyl ether), menthyl ester (e.g. menthyl formiate, menthyl acetate, menthyl isobutyrate, menthyl lactates, L-menthyl-L-lactate, L-menthyl-D-lactate, menthyl-(2-methoxy)acetate, menthyl-(2-methoxy ethoxy)acetate, menthyl pyroglutamate), N-(4-cyano methyl phenyl)-p-menthane carboxamide, N-(2-(pyridin-2-yl)ethyl)-3-p-menthane carboxamides, menthyl carbonates (e.g. menthyl propylene glycol carbonate, menthyl ethylene glycol carbonate, menthyl glycerine carbonate or mixtures thereof), menthane carboxylic acid amide (e.g. menthane carboxylic acid-N-ethylamid [WS3], N-alpha.-(menthane-carbonyl)glycine ethyl ester [WS5], menthane carboxylic acid-N-(4-cyanophenyl)amide, menthane carboxylic acid-N-(alkoxyalkyl) amide), menthone and menthone derivatives (e.g. L-menthone glycerine ketal), 2,3-dimethyl-2-(2-propyl)-butyric acid derivatives (e.g. 2,3-dimethyl-2-(2-propyl)-butyric acid-N-methyl amide [WS23]), isopulegol or its esters (1-(−)-isopulegol, 1-(−)-isopulegol acetate), menthane derivatives (e.g. p-menthane-3,8-diol), N-(4-cyano methyl phenyl)-p-menthane carboxamides, N-(2-(pyridin-2-yl)ethyl)-3-p-menthane carboxamides, cubebol or synthetic or natural mixtures containing cubebol, pyrrolidone derivates of cycloalkyl dione derivatives (e.g. 3-methyl-2(1-pyrrolidinyl)-2-cyclopentene-1-one) or tetrahydropyrimidine-2-ones (e.g. Icilin or related compounds such as those described in WO 2004/026840), N-(4-cyano methyl phenyl)-p-menthane carboxamide, N-(2-(pyridin-2-yl)ethyl)-3-p-menthane carboxamides, menthyl ether (e.g. (I-menthoxy)-1,2-propanediol, (I-menthoxy)-2-methyl-1,2-propanediol), more polar menthyl esters (e.g. menthyl lactates, L-menthyl-L-lactate, L-menthyl-D-lactate, menthyl-(2-methoxy)acetate, menthyl-(2-methoxy ethoxy)acetate, menthyl pyroglutamate), menthyl carbonates (e.g. menthyl propylene glycol carbonate, menthyl ethylene glycol carbonate, menthyl glycerine carbonate), the semi-esters of menthols with a dicarboxylic acid or the derivatives thereof (e.g. mono-menthyl succinate, mono-menthyl glutarate, mono-menthyl malonate, O-menthyl succinic acid ester-N,N-(dimethyl)amide, O-menthyl succinic acid ester amide), 3,4-methylendioxycinnamic acid-N-cyclohexyl-N-2-pyridylamide, isopropyl-(5-methoxy-2-pyridin-2-yl-pyrimidin-4-yl)-amine, 3,4,6,7,11b,12-hexahydro-3,3-dimethyl-spiro[13H-dibenzo[a,f]quinolizine-1-3,2'-[1,3]dithiolan]-1(2H)-one, 5,6,10b,11-tetrahydro-3-methyl-spiro[12H-benzo[a]furo[3,4-f]quinolizine-1-2,2'-[1,3]dithiolan]-1(3H)-one. Most preferred as cooling compounds are compounds selected from the group consisting of 5-methyl-2-(propane-2-yl)cyclohexyl-N-ethyloxamate, N-ethyl-p-menthane carboxamide (WS-3, also referred to as menthane-3-carboxylic acid-N-ethyl amide), menthyl lactate (Frescolat® ML), menthone glycerine acetal (Frescolat® MGA), N-(4-cyano methyl phenyl)-p-menthane carboxamide and (I-menthoxy)-1,2-propanediol.

Uses, Methods, and Flavored Products

In at least another aspect, the disclosure provides uses of the taste-modifying composition of the preceding aspects and embodiments thereof to reduce an off taste of a flavored product.

In related aspects, the disclosure provides methods for reducing an off taste of a flavored product, the method comprising introducing a taste-modifying composition of the preceding aspects and embodiments thereof to a flavored product.

In connection with these aspects, the flavored product can be any flavored product according to the aspects and embodiments set forth below. In some embodiments, the flavored product is a beverage product, such as enhanced sparkling beverages, colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies. In some other embodiments, the flavored product is a food product, such as a packaged meals, canned foods, meal replacement products, and the like. In some embodiments, the flavored product is an oral care product, such as a toothpaste, a mouthwash, or a teeth-whitening composition, such as a composition disclosed in U.S. Patent Application Pub. No. 2019/0167545, which is incorporated herein by reference.

In some embodiments, the flavored article comprises an alkali metal salt of peroxymonosulfate, such as potassium peroxymonosulfate. In embodiments in which the taste-modifying composition of the preceding aspects is incorporated or introduced into a flavored product, its concentration is such that the sum of all components of classes (a), (b), (c), and (d) have a concentration ranging from 10 ppm to 4000 ppm, or from 20 ppm to 3000 ppm, or from 30 ppm to 2500 ppm, or from 50 ppm to 2000 ppm, or from 100 ppm to 1500 ppm, where "ppm" is measured on a weight/weight basis, based on the total weight of the flavored product. In embodiments where only (a) and (b) are present, the concentrations are adjusted accordingly, such as from 10 ppm to 800 ppm, or from 20 ppm to 600 ppm, or from 30 ppm to 500 ppm, or from 50 ppm to 400 ppm, or from 100 ppm to 300 ppm, where "ppm" is measured on a weight/weight basis, based on the total weight of the flavored product. In embodiments where an alkali metal salt of peroxymonosulfate is present, such as potassium peroxymonosulfate, the concentration ratio (w/w) of the alkali metal salt of peroxymonosulfate to the sum of all components of classes (a), (b), (c), and (d) ranges from 25:1 to 10,000:1, or from 50:1 to 8000:1, or from 100:1 to 7000:1, or from 200:1 to 6000:1. Other non-limiting examples of alkali metal peroxymonosulfates include lithium peroxymonosulfate and sodium peroxymonosulfate.

In some embodiments, additional salts can also be present in the flavored product. For example, in some embodiments, the flavored product comprises potassium hydrogen sulfate and potassium sulfate.

The flavored product can be in any suitable physical form. For example, in some embodiments, the flavored composition can be in the form of a solid, such as a powder. In a further such embodiment, the flavored product is a toothpowder, such as a toothpowder for whitening teeth, removing stains (e.g., tobacco stains), and the like. In some other embodiments, the flavored product can be a paste or a slurry, such as a tooth paste. In some other embodiments, the flavored product can be in the form of a cream or gel, such as a tooth gel, a skin cream or tooth cream. In some other embodiments, the flavored product can be a liquid suspension or solution, for example, with an aqueous carrier. The flavored product can, in some embodiments, be in the form of an emulsion, such as a microemulsion or nanoemulsion, where a surfactant, emulsifier, and the like can be present. In some embodiments, the flavored product is a personal care, such as a product for application onto skin, face, lips, gums, mouth, and the like. Such personal products can be for any suitable use, such as skin whitening, teeth whitening, and the like.

In certain aspects, the disclosure provides flavored products comprising any compositions of the preceding aspects or embodiments thereof. In some embodiments, the flavored products are beverage products, such as soda, flavored water, tea, and the like. In some other embodiments, the flavored products are food products, such as yogurt.

In embodiments where the flavored product is a beverage, the beverage may be selected from the group consisting of enhanced sparkling beverages, colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies. In some embodiments, the beverage may be a soft drink.

In some embodiments, the flavored product is an oral care product. By "oral care product" is meant a personal care product or other product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, mouthspray, lozenge, chewable tablet, chewing gum or denture product. The oral care composition may also be incorporated onto strips or films for direct application or attachment to oral surfaces.

In some embodiments, the flavored product is a pharmaceutical product, such as a product designed to carry or deliver certain active pharmaceutical ingredients (APIs). Such APIs can be over-the-counter (OTC) drugs, such as acetaminophen and other OTC cough and cold medications. In some embodiments, the API is a prescription-based drug.

In certain embodiments of any aspects and embodiments set forth herein that refer to a flavored product, the flavored product is a non-naturally-occurring product, such as a packaged food or beverage product.

Further non-limiting examples of food and beverage products or formulations include sweet coatings, frostings, or glazes for such products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionery category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionery category generally refers to edible product that is sweet to the taste. Examples of confectionery include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles. The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for flavored products, particularly food and beverage products or formulations, are provided as follows. Exemplary ingestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary ingestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary ingestible compositions also include breakfast cereals, sweet beverages or solid or liquid concentrate compositions for preparing beverages, ideally so as to enable the reduction in concentration of previously known saccharide sweeteners, or artificial sweeteners.

Some embodiments provide a chewable composition that may or may not be intended to be swallowed. In some embodiments, the chewable composition may be gum, chewing gum, sugarized gum, sugar-free gum, functional gum, bubble gum including compounds as disclosed and described herein, individually or in combination.

In some embodiments, the taste-modifying compositions as disclosed and described herein, individually or in combination, may be provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g., any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacturer in large industrial scales to produce the ready-to-use soft drinks. Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

The flavored products set forth according to any of the foregoing embodiments, also include, in certain embodiments, one or more additional flavor-modifying compounds, such as compounds that enhance sweetness (e.g., hesperetin, naringenin, glucosylated steviol glycosides, etc.), compounds that block bitterness, compounds that enhance umami, compounds that reduce sourness, compounds that enhance saltiness, compounds that enhance a cooling effect, or any combinations of the foregoing.

In certain embodiments of any aspects and embodiments set forth herein that refer to a sweetening or flavoring concentrate, the sweetening or flavoring concentrate is a non-naturally-occurring product, such as a composition specifically manufactured for the production of a flavored product, such as food or beverage product.

In one embodiment, the flavoring concentrate formulation comprises i) compounds as disclosed and described herein, individually or in combination; ii) a carrier; and iii) optionally at least one adjuvant. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the content of which is hereby incorporated by reference in its entirety for all purposes.

In one embodiment, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. In some embodiments, the present flavoring concentrate formulation can be carbonated or non-carbonated.

The flavoring concentrate formulation may further comprise a freezing point depressant, nucleating agent, or both as the at least one adjuvant. The freezing point depressant is an ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes an ingestibly acceptable compound or agent which is able to facilitate nucleation. The presence of nucleating agent in the flavoring concentrate formulation can improve the mouthfeel of the frozen Blushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

EXAMPLES

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Example 1—Sample Toothpaste Formulation

Toothpaste formulations are made that incorporate taste-modifying compositions according to certain embodiments of the present disclosure. Table 1 below sets forth a list of ingredients for inclusion in the taste-modifying composition, as well as their recommended concentration when incorporated into a toothpaste.

TABLE 1

| Ingredient | Conc (wt. %) |
|---|---|
| 4-Amino-5,6-dimethylthieno[2,3-d]pyrimidin-2(1H)-one, HCl salt (A) | 0.0160 |
| Dihydromintlactone | 0.0000-0.0055 |
| Glucosylated natural steviol glycoside* (C) | 0.0100 |
| Surcralose (D) | 0.1000 |

*The glucosylated natural steviol glycoside is GSG NSF-02 from PureCircle, which has degree of glucosylation of 2.36, and contains alpha-1,6 linkages.

Note that the four ingredients above are labeled from (A) to (D). Table 2 below shows a variety of alternative embodiments of toothpaste formulations that can be made. The amounts are reported in percent by weight, based on the total weight of the toothpaste composition. Note the other ingredients are labeled as follows.

(E) WNQ-14-001 Tooth Paste Base (F) Potassium Peroxymonosulfate (G) Mint flavor (H) Sodium saccharin

TABLE 2

| | T1 | T2 |
|---|---|---|
| A | — | 0.0160 |
| B | — | 0.0055 |
| C | — | 0.0100 |
| D | 0.100 | 0.100 |
| E | 97.00 | 96.96 |
| F | 1.00 | 1.00 |
| G | 1.10 | 1.10 |
| H | 0.800 | 0.800 |

Example 2—Sensory Testing

Various compositions were tested by a panel of sensory testers. Each of the test compositions T1 and T2 was tested by panelists, who were asked to evaluate its off taste on a scale from 1 to 5, with 5 being comparable to the T1 composition and 1 being no off taste at all. Table 3 presents the results.

TABLE 3

| Sample | Rating (1-5) |
|---|---|
| T1 | 5 |
| T2 | 2.5 |

The invention claimed is:

1. A method for reducing an off taste, wherein the off taste is the off taste of potassium peroxymonosulfate, of a flavored product, wherein the flavored product is a toothpaste, the method comprising introducing a taste-modifying composition comprising: (a) 4-amino-5,6-dimethylthieno-[2,3-d]pyrimidin-2(1H)-one, or a salt thereof; (b) a lactone, wherein the lactone is dihydromintlactone; and (c) glucosylated natural steviol glycosides to the flavored product comprising sucralose, mint flavor, saccharin, and potassium peroxymonosulfate, wherein the concentration of the taste-modifying composition is such that the total concentration of compounds (a), (b), and (c) range from 5 to 500 ppm, based on the total weight of the flavored product, wherein the weight-weight ratio of compound (b) and compound (c) ranges from 1:3 to 1:1.

2. The method of claim 1, wherein the flavored product further comprises potassium hydrogen sulfate, potassium sulfate, or a combination thereof.

3. The method of claim 1, wherein the taste-modifying composition further comprises a cooling enhancing compound.

4. The method of claim 3, wherein the cooling enhancing compound is a compound selected from the group consisting of:

N-ethyl-N-(thiophen-2-ylmethyl)-2-(p-tolyloxy)acetamide;

N-(1H-pyrazol-3-yl)-N-(thiophen-2-ylmethyl)-2-(p-tolyloxy)acetamide;

2-(4-fluorophenoxy)-N-(1H-pyrazol-3-yl)-N-(thiophen-2-ylmethyl)acetamide;

2-(2-hydroxy-4-methylphenoxy)-N-(1H-pyrazol-3-yl)-N-(thiophen-2-ylmethyl)-acetamide;

2-((2,3-dihydro-1H-inden-5-yl)oxy)-N-(1H-pyrazol-3-yl)-N-(thiophen-2-ylmethyl)-acetamide;

2-((2,3-dihydro-1H-inden-5-yl)oxy)-N-(1H-pyrazol-3-yl)-N-(thiazol-5-ylmethyl)-acetamide; and 2-((5-methoxybenzofuran-2-yl)oxy)-N-(1H-pyrazol-3-yl)-N-(thiophen-2-ylmethyl)-acetamide.

* * * * *